April 22, 1969 J. W. PATTERSON Plant Pat. 2,881
ROSE PLANT
Filed March 3, 1967
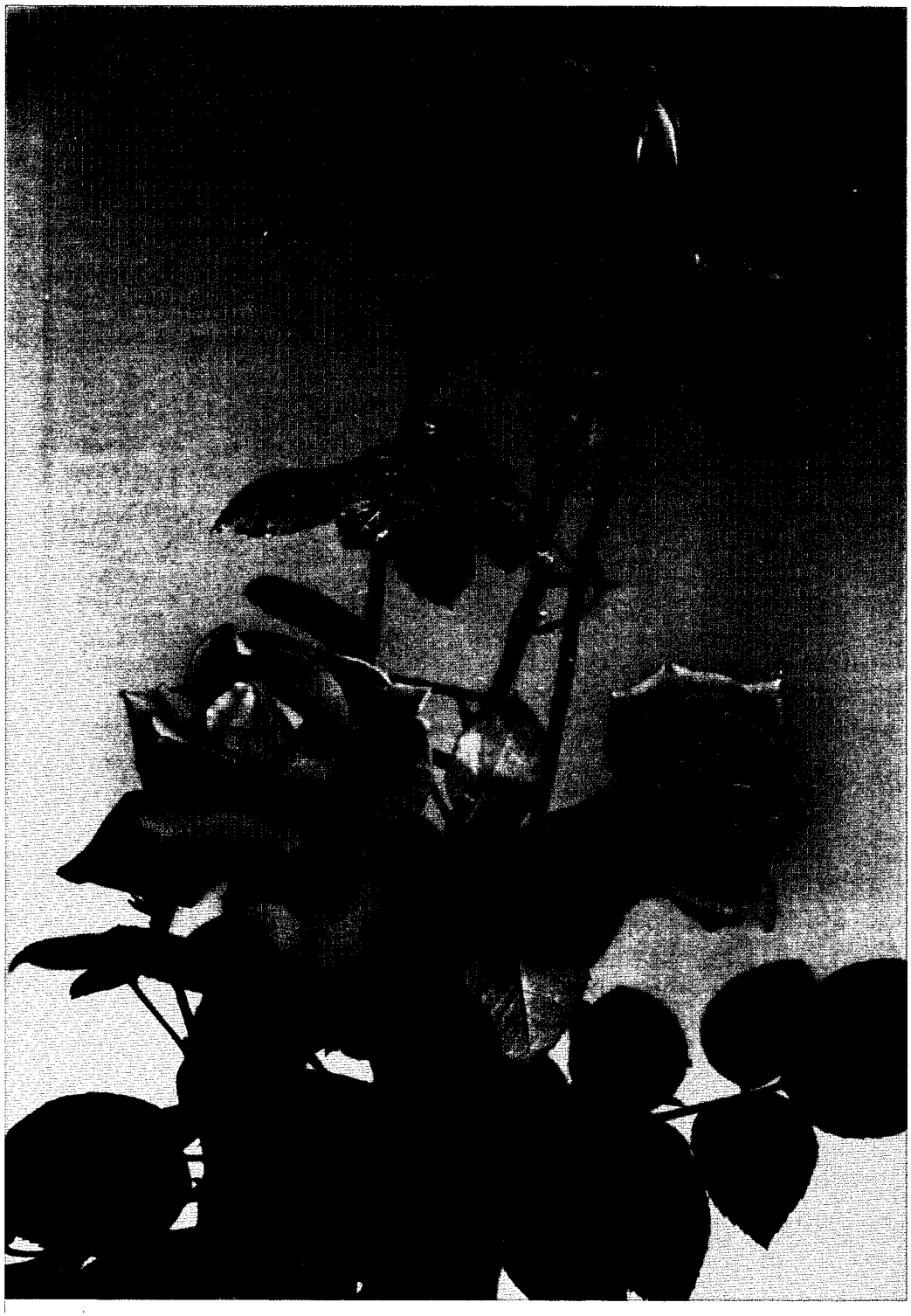

United States Patent Office

Plant Pat. 2,881
Patented Apr. 22, 1969

2,881
ROSE PLANT

John W. Patterson, 6518 Kernel,
Houston, Tex. 77017

Filed Mar. 3, 1967, Ser. No. 620,549
U.S. Cl. Plt.—21 1 Claim

The present invention relates to a new and distinct variety of rose plant of the hybrid tea class, which was originated by me by crossing the variety "Red Jacket" (Plant Patent No. 968) with the variety "Mirandy" (Plant Patent No. 632).

The primary objective of this breeding was to produce a new rose variety which bears flowers of improved color and number of petals, also to improve the longevity of cut flowers and to produce a stronger stem. The objectives were substantially achieved by the following characteristics which are outstanding in the new variety and which distinguish it from its parents, as well as from all other varieties of which I am aware:

(1) Good growing, upright habits;

(2) Relatively large flowers which are borne on strong stems;

(3) Very strong, spicy fragrance;

(4) Good flower form;

(5) Good keeping qualities of flowers as cut flowers;

(6) A distinctive attractive general color tonality of flowers corresponding to Garnet Lake in newly opened flowers.

In comparison with its seed parent, "Red Jacket," the new variety is more disease resistant; flowers are borne on strong stems and are more fragrant; flowers are darker in color and have better keeping qualities as cut flowers.

As compared with its pollen parent, the new variety has a stronger flower stem and is a better flower producer.

Asexual reproduction of my new variety by budding at Houston, Tex., and also at Tyler, Tex., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society:

Type: Bush; seedling.
Class: Hybrid tea.
Breeding: Seedling.
*Seed parent.*—"Red Jacket."
*Pollen parent.*—"Mirandy."
Propagation: Holds its distinguished characteristics through succeeding propagations by budding.

*Flower*

Locality where grown and observed: Houston, Tex.
Blooming habit: Recurrent—continuous through growing season.
Flowers borne: Singly to stem (occasionally more than one); on strong stems of medium length.
Quantity of bloom: Abundant, outdoors.
Frangrance: Very strong, spicy.
Bud:
*Peduncle.*—Long; strong. Bark moderately smooth.
*Color.*—Scheeles Green, Plate 860/1, page 175.
*Before calyx breaks.*—Size—medium to large. Form—long, pointed; with foliaceous apendages on the surface of the bud. Color—near Scheeles Green, Plate 860/2, page 175.

*As calyx breaks.*—Color (outside of petal)—Ruby Red, Plate 827/1, page 171. Sepals—inner surface with fine wooly tomentum. Outside surface—color—Scheeles Green, Plate 860/2, page 175, slightly overcast with Garnet Lake, Plate 828/1, page 172.
*As first petal opens.*—Size—average to large for class. Form—long length; globular. Color: outside—base of petal Indian Lake, Plate 826, page 170, changing to near Garnet Lake, Plate 828, page 172; inside—Garnet Lake, Plate 828, page 172, top tip of petal near Dahlia Purple, Plate 931, page 178.
*Opening.*—Opens slowly, keeping shape well; no unusual characteristics attributed to weather conditions.
Bloom:
*Size (when fully open).*—Large; from 4½ inches to 5 inches.
*Petalage.*—Double; from 40 to 50 petals; arranged regularly.
*Form.*—Full and high-centered.
Petals:
*Texture.*—Thick, slightly velvety both inside and outside.
*Shape.*—Outer—obovate; intermediate—obovate; inner—obovate.

This description of a newly opened flower was made from a rose grown outside during the month of November at Houston, Tex.

*Color.*—Outer petal: outside surface—near Garnet Lake, Plate 282/2, page 172; inside surface—Garnet Lake, Plate 828, page 172; ⅓ petal at base Garnet Lake, Plate 828/2, page 172. Intermediate petal: outside surface—near Garnet Lake, Plate 828, page 172; inside surface—lower ⅓ petal at base Garnet Lake, Plate 828/1, page 172, upper ⅔ petal near Garnet Lake, Plate 828, page 172. Inner petal: outside surface—Garnet Lake, Plate 828/3, page 172; inside surface—near Garnet Lake, Plate 828, page 172. Base of petal lighter in color with a small tip of white at extreme base.

This description was made from a rose that was open for three days outside during the month of November at Houston, Tex.

*Color.*—Outer petal: outside surface—Indian Lake, Plate 826/2, page 170; inside surface—Indian Lake, Plate 826, page 170. Intermediate petal: outside surface—Ruby Red, Plate 827/3, page 171; inside surface—Ruby Red, Plate 827/2, page 171. Inner petal: outside surface—near Ruby Red, Plate 827/1, page 171; inside surface—Ruby Red, Plate 827, page 171.
*General color effect.*—Newly opened flower—Garnet Lake, Plate 828, page 172. Three days open—near Ruby Red, Plate 827/1, page 171.
*Behavior of petals.*—Drop off cleanly; color sometimes darkens with age.
*Flower longevity.*—On bush in garden in November 4 or 5 days. Cut roses grown outdoors and kept at living-room temperatures 4 days.

*Reproductive organs*

Stamens: Many; arranged irregularly about pistils; mixed with petaloids.
Filaments: Some short and some medium length; most with anthers. Color—Magenta Rose, Plate 027/1, page 113.
Anthers: Medium size; open at various times. Color—Yellow Ochre, Plate 07/2, page 101.

Pollen: Very sparse. Color—Saffron Yellow, Plate 7/2, page 7.
Pistils: Average amount.
Styles: Short, uneven and bunched.
Stigma: Color—near Brick Red, Plate 016/2, page 106.
Ovaries: All enclosed in receptacle.
Hips: None observed.
Sepals: Permanent; long; spear shaped. Color: inside—Scheeles Green, Plate 860, page 175, overlaid with white fuzz; outside—Spinach Green, Plate 0960/1, page 187.
Seeds: None.

*Plant*

Foliage:
*Leaves.*—Compound of 5 leaflets; normal; medium size; leathery.
*Leaflets.*—Shape—ovate. Apex—acute. Base—round. Margin—serrate.
*Color.*—Mature: upper surface—near Scheeles Green, Plate 860, page 175; under surface—near Lavender Green, Plate 000761/1, page 196. Young: upper surface—Lettuce Green, Plate 861/1, page 176, slightly overlaid with Pansy Purple, Plate 928/3, page 177; under surface—Lettuce Green, Plate 861/3, overlaid with Pansy Purple, Plate 928/1, page 177.
*Rachis (the supporting stem of the compound leaf).*—Medium heavy. Upper side—grooved. Under side—smooth surface.

*Stipules.*—Medium length; medium width, with points turning out at more than 45° angle.
Growth:
*Habit.*—Bush; upright; compact.
*Growth.*—Vigorous.
*Canes.*—Medium diameter; strong.
*Main stems.*—Color—Spinach Green, Plate 0960/2, page 187. Thorns—few; medium length; hooked downward; color—Greyish brown (no color in chart listed). Prickles—many.
*Branches.*—Color—Spinach Green, Plate 0960/3, page 187. Thorns—few. Prickles—many.
*New shoots.*—Color—Scheeles Green, Plate 860/3, page 175. Thorns—several; short length; hooked downward; color—near Oxblood Red, Plate 00823/3, 191. Prickles—many; color—Oxblood Red, Plate 00823/3, page 191.

I claim:

1. A new and distinct variety of rose plant of the hybrid tea class, substantially as herein shown and described, characterized particularly as to novelty by the combination of good growing and flower producing habits, relatively large flowers which are borne on strong stems, good flower form, good flower fragrance, better than average disease resistance, attractive dark red color corresponding to Garnet Lake, and good keeping qualities of the flowers as cut flowers.

No references cited.

ROBERT E. BAGWILL, *Primary Examiner.*